United States Patent [19]

Schmid

[11] Patent Number: 4,643,649

[45] Date of Patent: Feb. 17, 1987

[54] DIGITAL CONTROL FOR RAPID REFILL OF A LIQUID CHROMATOGRAPH PUMP

[75] Inventor: Carl E. Schmid, Easton, Conn.

[73] Assignee: The Perkin-Elmer Corporation, Norwalk, Conn.

[21] Appl. No.: 700,785

[22] Filed: Feb. 11, 1985

Related U.S. Application Data

[63] Continuation-in-part of Ser. No. 632,758, Jul. 20, 1984, Pat. No. 4,556,367, and a continuation-in-part of Ser. No. 343,807, Jul. 29, 1982, abandoned.

[51] Int. Cl.[4] ............................................. F04B 49/06
[52] U.S. Cl. ........................................... 417/45; 417/53
[58] Field of Search ..................... 417/18, 22, 42, 43, 417/44, 45, 53

[56] References Cited

U.S. PATENT DOCUMENTS

| | | | |
|---|---|---|---|
| 3,847,507 | 11/1974 | Sakiyama et al. | 417/45 X |
| 4,131,393 | 12/1978 | Magnussen, Jr. | 417/45 X |
| 4,137,011 | 1/1979 | Rock | 417/22 |
| 4,225,290 | 9/1980 | Allington | 417/18 |
| 4,326,837 | 4/1982 | Gilson et al. | 417/45 X |
| 4,352,636 | 10/1982 | Patterson et al. | 417/22 |
| 4,359,312 | 11/1982 | Funke et al. | 417/18 |
| 4,474,309 | 10/1984 | Solomon | 417/22 X |
| 4,552,513 | 11/1985 | Miller et al. | 417/18 |

FOREIGN PATENT DOCUMENTS 156285  12/1980  Japan ...................... 417/42

Primary Examiner—Carlton R. Croyle
Assistant Examiner—Paul F. Neils
Attorney, Agent, or Firm—Ronald G. Cummings; Francis L. Masselle; Edwin T. Grimes

[57] ABSTRACT

A liquid pump motor control for a liquid chromatograph. The control detects when the pump needs to be refilled. Then, the pump motor is accelerated at a first rate for a given number of pulses. Then the motor is accelerated at substantially its maximum rate until a selected maximum speed is reached. Thereafter the speed is maintained at its maximum until the time calculated to begin deceleration. The motor is then decelerated substantially at its maximum deceleration rate until the speed is close to the final desired speed. Then deceleration occurs at a slower rate for a fixed number of pulses. The number of pulses applied to the stepping motor from the beginning of acceleration until the end of deceleration is constant regardless of the beginning or ending pulse rates.

22 Claims, 6 Drawing Figures

| | | | |
|---|---|---|---|
| T0 – T1 | A(1) = 94550 STEP/SEC² | 3 STEPS | T0 = 0 |
| T1 – T2 | A(2) = 293105 STEP/SEC² | 51 STEPS | T1 = 5.81545 ms |
| T2 – T3 | A(3) = 0 STEP/SEC² | 100 STEPS | T2 = 21.8321 ms |
| T3 – T4 | A(4) = –320,000 STEP/SEC² | 46 STEPS | T3 = 40.1317 ms |
| T4 – T5 | A(5) = –57811 STEP/SEC² | 6 STEPS | T4 = 54.6097 ms |
| | | | T5 = 65.44 ms |

| | | |
|---|---|---|
| SPEED AT T0 | 240.942 | STEPS/SEC |
| SPEED AT T1 | 790.793 | STEPS/SEC |
| SPEED AT T2 | 5500 | STEPS/SEC |
| SPEED AT T3 | 5500 | STEPS/SEC |
| SPEED AT T4 | 867.055 | STEPS/SEC |
| SPEED AT T5 | 240.942 | STEPS/SEC |

*TABLE 1*

TABLE 2

| | | | | | |
|---|---|---|---|---|---|
| T0-T1 | A(1) = 94550 | STEP/SEC² | 3 STEPS | T0 = 0 | SPEED AT T0 2409.42 STEPS/SEC |
| T1-T2 | A(2) = 293105 | STEP/SEC² | 41 STEPS | T1 = 1.21609 ms | SPEED AT T1 2524.4 STEPS/SEC |
| T2-T3 | A(3) = 0 | STEP/SEC² | 119 STEPS | T2 = 11.3681 ms | SPEED AT T2 5500 STEPS/SEC |
| | | | | T3 = 33.033 ms | SPEED AT T3 5500 STEPS/SEC |
| T3-T4 | A(4) = -320,000 | STEP/SEC² | 37 STEPS | T4 = 42.2539 ms | SPEED AT T4 2549.32 STEPS/SEC |
| T4-T5 | A(5) = -57811 | STEP/SEC² | 6 STEPS | T5 = 44.6739 ms | SPEED AT T5 2409.42 STEPS/SEC |

DIGITAL CONTROL FOR RAPID REFILL OF A LIQUID CHROMATOGRAPH PUMP

This is continuation-in-part of application Ser. No. 632,758, filed July 20, 1984, now U.S. Pat. No. 4,556,367, and application Ser. No. 343,807, filed July 29, 1982, now abandoned.

FIELD OF THE INVENTION

The present invention relates broadly to the field of liquid chromatography and more particularly to a pump and control circuitry associated therewith for maintaining substantially constant fluid flow in the column of a liquid chromatogram.

BACKGROUND OF THE INVENTION

In the broad field of analytical instruments, chromatographs have been used to separate and measure the concentration of the constituents of complex mixtures. In liquid chromatography, an unknown sample is injected into a column having a flowing liquid therein consisting of one or more liquid solvents. A detector at the base of the column detects the presence of the constituents as they appear or elute from the bottom of the column. A plot of the detector output as a function of time, known as a chromatogram, is used by the chromatographer in his analysis of the unknown sample.

For example, it may be desired to know the concentration of a given medication in the blood stream of a patient. A known volume of blood would be entered into a chromatographic column and the constituent parts including the drug fraction would then separate out and be detected. The peak area of the chromatogram would indicate the concentration of each component while the elution time would identify the specific drug. From that, the percentage of medication in the blood can be calculated.

Typical liquid chromatographs have liquid pumps for delivering the column solvent with the unknown sample injected into the column liquid. Due to the volume of liquid that flows through the column during the length of an experiment, the pump for the column liquid must be designed to refill and resume pumping a great number of times during an experiment. In addition, some means is required to maintain the column flow at as uniform a level as possible over the entire experiment.

One approach to accomplishing this is to use two synchronized pumps with one pump being operative to deliver liquid to the column while the other is refilling. This arrangement, however, is quite expensive because of the requirement of having two pumps for each liquid in the column. In multi-solvent liquids, two such pumps are needed for each solvent. Clearly, for chromatographs that proportion up to 4 different solvents, the cost of having 8 pumps is very high and they are difficult to synchronize with each other.

A better approach is found in the pump used in the Perkin-Elmer Series 4 Liquid Chromatograph. In that instrument, the pump includes two synchronized pistons. One serves as a metering pump and the other a delivery pump. While the delivery pump is pumping liquid to the column, the metering pump is filled with the proper mixture of a plurality of solvents. Once the delivery pump is empty, the pump motor speeds up under control of an analog circuit and a specially shaped cam driven thereby causes the liquid in the metering pump to be quickly transferred to the delivery pump. Thereafter, the motor is slowed by the analog circuit and the delivery pump resumes pumping liquid to the column. A pressure damper is utilized to maintain column pressure, during the delivery pump refill, as uniform as possible.

This type of pumping arrangement does permit a good deal of control over maintaining uniform column flow during the delivery pump refill. However, even with appropriate size pressure dampers, the fluid pressure at the column does change somewhat during the delivery pump refill.

Additional problems with the analog control circuitry include: 1. high cost due to high analog circuit count, 2. the analog circuit is difficult to adjust and once adjusted is optimum for only one flow rate, 3. the analog circuit does not maintain accurate phase relationship with the cam position, and 4. analog circuits are sensitive to temperature and component drift.

It is, therefore, the principal objective of the present invention to provide a rapid refill control for a liquid chromatograph pump which permits maintenance of more uniform column flow than has been achieved in prior art devices mentioned above.

It is a further objective to provide a rapid refill control for a liquid chromatograph which adjusts automatically to flow rate changes to keep pressure changes at the column to a minimum.

It is still a further objective of the present invention to provide a rapid refill control with the above mentioned objectives at a cost which is lower than the cost for the analog circuits used in the prior art instrument.

BRIEF DESCRIPTION

The foregoing and additional objectives are achieved by the digital control circuit of the present invention. A sensor is provided to detect the position of the pump cam. At an appropriate time the control circuit of the present invention starts to slowly accelerate the pulse rate of the pulses applied to the cam and pump driving motor. The first rate of acceleration is maintained for a selected number of pulses and then the pulse rate accelerates at a faster rate until the motor achieves maximum speed. The control circuit maintains maximum speed until the appropriate time and then begins to rapidly decelerate. Deceleration occurs at a rapid constant rate until the motor speed is near that of the desired speed for delivery pump operation. Then the deceleration continues at a slower rate until the motor reaches its final desired velocity which is selected to maintain the desired liquid flow rate in the column.

BRIEF DESCRIPTION OF THE DRAWINGS

The foregoing and other objects, advantages and features of the present invention are described below in greater detail in connection with the drawings which form a part of the disclosure wherein.

DETAILED DESCRIPTION

Figure 1A:
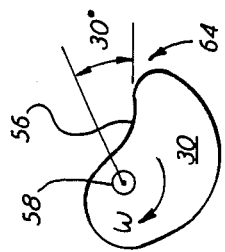
FIG. 1A is an illustration of the cam used in the pump of FIG. 1.
Figure 1:
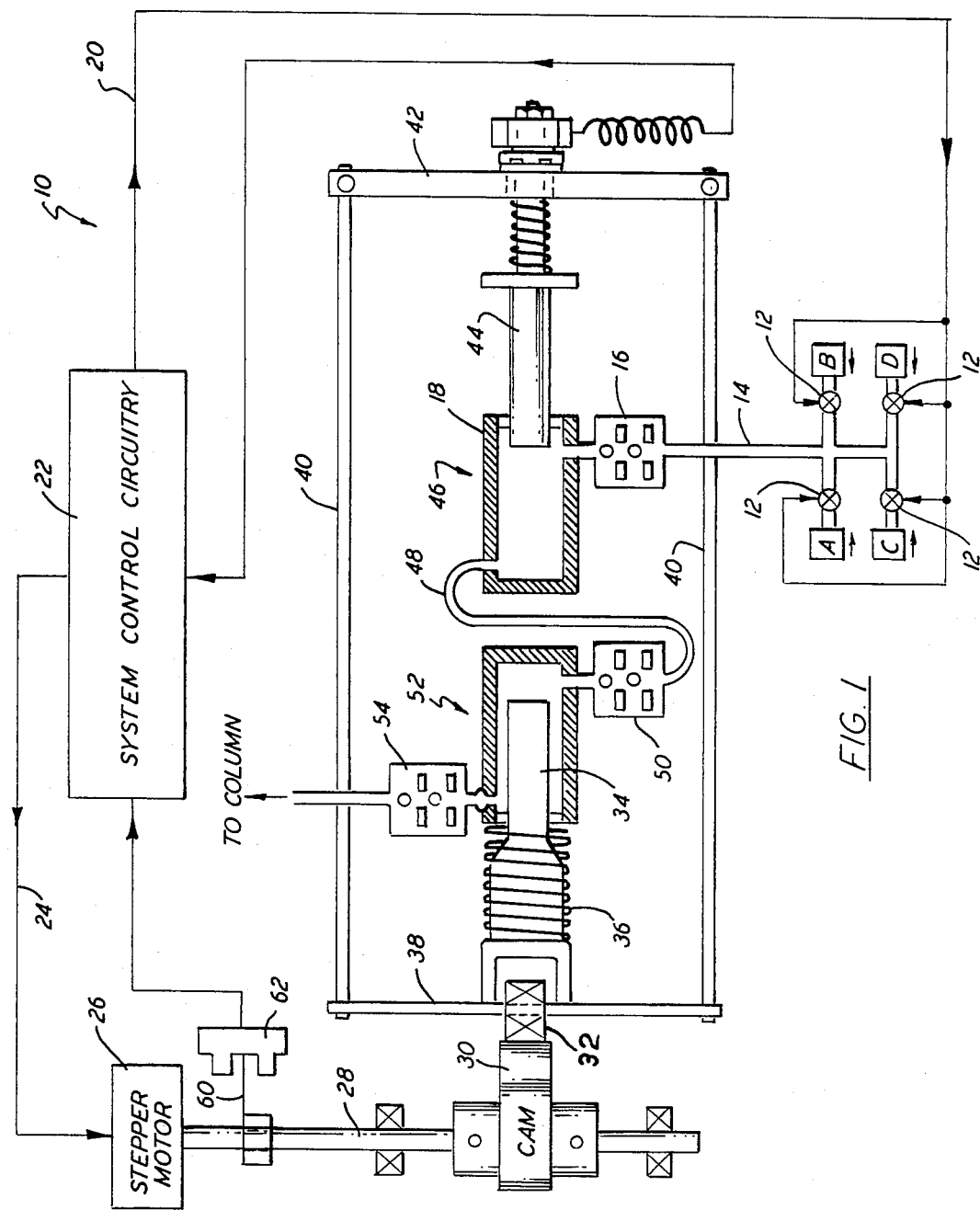
FIG. 1 is a block diagram of the liquid chromatograph pump of the present invention.

The fluid delivery system 10 of a liquid chromatograph in accordance with the present invention is schematically illustrated in FIG. 1. The fluid delivery system 10 is capable of supplying a precise mixture of a plurality of solvents to the column of the chromatograph. The solvent supply sources are illustrated by the boxes labeled A, B, C and D. It should be mentioned, however, that the number of solvent supplies is immaterial to the specifics of the present invention and that if adequate controls are available, either more or fewer solvents could be delivered in mixture to the column.

A plurality of electrically controlled valves 12 are located between the solvent supplies A, B, C and D and a delivery tube 14 which couples via a check valve 16 to a metering pump cylinder 18. The control valves 12 are opened and closed by signals received over the line 20 from the system control circuitry 22. The portion of the system control circuitry 22 which is operable to control the valves 12 is of the type generally described in U.S. Pat. No. 4,450,574 which is assigned to the same assignee as this application and is herein, in its entirety, incorporated by reference.

The system control 22 provides stepping pulses over the line 24 to the stepper motor 26. As the stepper motor rotates, this rotary motion is transmitted by an axle member 28 to a cam 30 mounted on the axle 28. A cam follower 32 rides on the surface of the cam 30 as it turns. The cam follower is mechanically coupled to the delivery piston 34 and stays in contact with the cam surface because a return spring 36, always in compression, forces the cam follower 32 in a direction toward the surface of the cam 30. The cam follower 32 is coupled by arm members 38, 40 and 42 to the piston of the metering pump 44. By this arrangement, when the cam follower 32 moves in a leftward direction as illustrated in FIG. 1, the delivery piston 34 moves in a leftward direction as does the piston 44 of the metering pump 46. When this occurs, fluid is transferred from the metering pump 46 via the pipe 48 and check valve 50 to the delivery pump 52. In this manner, when the delivery pump 52 no longer has fluid in it, the piston 34 is moved in a leftward direction and fluid is transferred quickly from the metering pump 46 to fill the void caused by withdrawal of the piston 34. Thereafter, as the piston 34 moves in a rightward direction, the liquid in the pump 52 is forced through the check valve 54 into a delivery conduit which couples to the chromatograph column. At the same time, the piston 44 is moved in a rightward direction and the metering pump 46 is filled via the delivery tube 14 and check valve 16 from the solvent supplies A, B, C and D with the desired mix of solvents.

The cam 30 has a profile substantially as shown in FIG. 1A. The cam has a portion of its exterior surface 56 where the distance between the rotational axis of the cam 58 and the surface of the cam changes very rapidly with only a small change of rotation about the axis 58. Indeed, the distance between the axis and the cam surface changes over approximately 30 degrees of rotation from its maximum to its minimum. Accordingly, with proper synchronization of the cam 30 with the operation of the pumps 52 and 46 as well as with the valves 12, the metering pump 46 can be emptied very rapidly during the 30 degrees rotation of the cam so that delivery from the delivery pump 52 can proceed over approximately 330 degrees of rotation of the cam 30. In this manner, the delivery pump 52 is pumping fluid to the column for substantially the majority of the rotation of the cam 30. This is desirable because it maintains a substantially constant flow rate over the entire cycle with the flow being interrupted only during the short period of time required to refill the delivery pump 52.

In accordance with the principles set forth in copending U.S. patent application Ser. No. 632,758, filed July 20, 1984, now U.S. Pat. No. 4,556,367, the entire content of which is herein incorporated by reference, the time required to accomplish the refill function (transfer of fluid from the metering pump 46 to the delivery pump 52) and the accuracy of the refill can be improved by adapting the system control circuitry 22 of the present invention to respond to a flag 60 mounted on the axle member 28 to accelerate the pulse rate over line 24 to the stepper motor 26 in two phases. Once the stepper motor 26 reaches a desired maximum speed, the stepper motor is maintained at that rate by pulses from the system control circuitry 22. When the proper time comes, the system control circuitry 22 causes the stepper motor 26 to decelerate in two phases to a speed commensurate with that used during delivery of fluid from the pump 52 to the column. Accordingly, not only is the refill of the delivery pump 52 accomplished quickly by reason of the fact that the cam 30 has the shape as illustrated in FIG. 1A but also the cam 30 is turned faster during the refill. However, since the stepping motor 26 speeds up and subsequently slows down during the time frame when the cam rotates through the 30 degrees of rapidly falling radius, the portion of a full cycle time devoted to refilling the delivery pump 52 is reduced from what it would be if the system control circuitry 22 did not produce stepping motor control pulses at an elevated rate from that when the delivery pump 52 is actually pumping fluid to the column.

Figure 2:
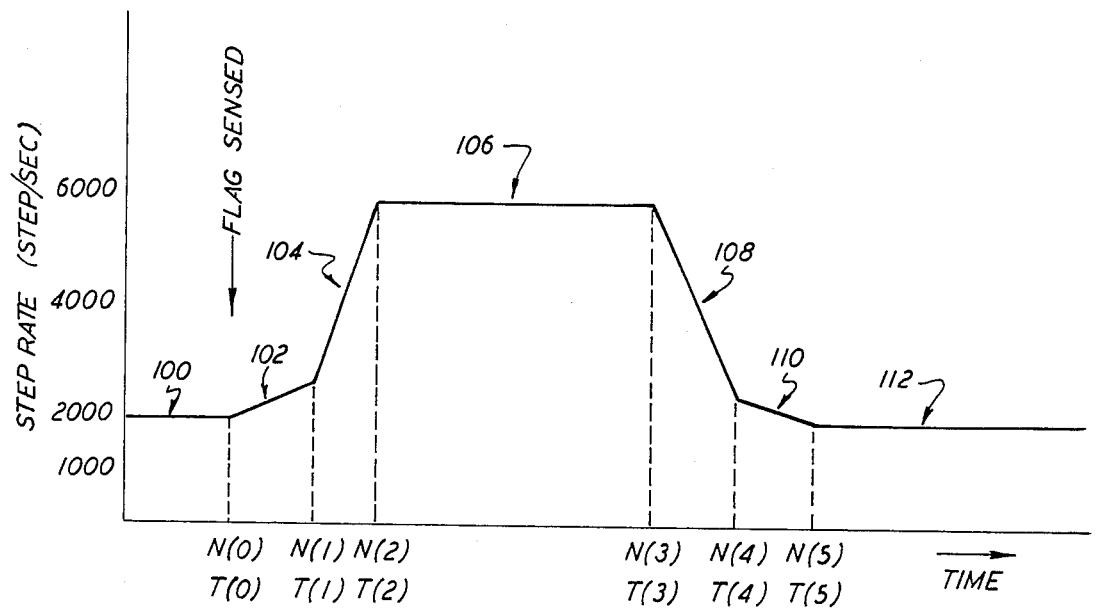
FIG. 2 is a graph showing the typical pulse rate of pulses, as a function of time, applied to the stepping motor of FIG. 1 during the rapid refill operation.

Referring now to FIG. 2, a graph is shown which plots the pulse rate of signals applied to the stepping motor 26 of FIG. 1. In the region indicated generally at 100, the stepping motor 26 at a flow rate of 10 ml/min receives pulses at a rate in the preferred embodiment of about 2,000 pulses per second. At the time when the flag is sensed by the sensor 62, the system control 22 responds thereto to accelerate the pulse rate of the signals applied to the stepping motor 26 at a first rate. In FIG. 2, the flag 60 is detected at the time N(0) and the step rate accelerates at a gradual rate determined by the slope of the graph at 102. This gradual acceleration of the stepping motor 26 is desirable to make sure that the cam follower 32 gets over the hump on the cam indicated generally at 64 in FIG. 1A. Thereafter, at time T(1) the cam follower 32 is on the surface 56 of the cam 30 and the return spring 36 acts to keep the cam follower 32 in contact therewith and assists the motor in accelerating the cam. The stepping motor can then be accelerated at a second rate higher than the first rate as indicated by the slope of the graph generally at 104 in FIG. 2. The motor is accelerated during this second phase until it reaches a desired maximum speed which, for the illustration of FIG. 2, occurs at time T(2) when the stepping rate in the preferred embodiment is about 6,000 pulses per second. From time T(2) to T(3) the stepping rate for the motor 26 remains at 6,000 steps per second as illustrated at 106 in FIG. 2. At time T(3), the stepping motor 26 is slowed at a constant rate as determined by the slope of the graph as illustrated at 108 in FIG. 2. This deceleration continues until time T(4) at which time the deceleration rate is reduced and the step rate changes until it reaches the final stepping rate used during pumping of fluid from the delivery pump 52 to the column which occurs at time T(5). The slower deceleration rate is indicated by the slope of the graph generally at 110. The final stepping rate for the motor 26 during delivery of liquid to the column is illustrated at 112 and, for the preferred embodiment illustrated by FIG. 2, this stepping rate is approximately 2,000 steps per second at 10 ml/min.

As mentioned earlier, the acceleration of the stepping motor between time T(0) and T(1) ensures that cam follower 32 gets past the top of the cam 30 to a position where the return spring 36 is driving the cam follower 32 against the cam in such a way as to assist in accelerating the rotational speed of the cam 30. The rate of acceleration during this time period is defined as A(1) step/sec$^2$. The stepping motor 26 is accelerated at the rate of A(1) steps per sec$^2$ for N(1) steps after the flag is detected. The acceleration rate A(1) is selected to be somewhat below the maximum rate achievable by the stepping motor assuming the maximum load on the stepping motor prior to the cam follower reaching the point on the cam 30 of maximum radius. The number N(1) of steps is selected to assure that the cam follower has surely reached the rapidly decreasing radius as the cam 30 turns. This period of N(1) steps compensates for minor phase misalignment between the detection of the flag and the actual cam follower position. In the preferred embodiment where the cam 30 turns 360° in 1600 steps, N(1) steps is selected to be 3 steps and A(1) is about 94,550 steps/sec$^2$.

After N(1) steps have occurred, the rate of acceleration of the motor 26 is increased to A(2) step/sec$^2$ for the number of steps necessary to accelerate the motor from the speed achieved at time T(1) until the motor reaches the maximum speed as indicated at 106 at FIG. 2. The acceleration rate A(2) is selected in consideration with the stepping motor 26 and all of the elements mechanically coupled thereto so the motor will accelerate at its fastest possible rate until it reaches the maximum desired velocity. This acceleration rate A(2) must be determined in accordance with well known considerations on an individual basis for each mechanical configuration employing the concept of the present invention by the engineers designing systems of this type. For the preferred embodiment of the invention A(2) is about 293,105 steps/sec$^2$.

The maximum speed of the motor in the region indicated at 106 is determined by the motor characteristics itself. Above a certain speed, stepping motors typically lose torque and, therefore, are not suitable above those speeds. For the preferred embodiment, the maximum step rate is near 6,000 steps/sec.

The deceleration in the portion of the curve indicated at 108 is selected considering the maximum deceleration of the system including the motor and the mechanical elements coupled thereto. The time at which this maximum deceleration begins is determined by the system control circuitry. The calculation is quite simply made because the total number of steps for the stepping motor 26 is fixed for the sum of the segments of time involving the acceleration, the high speed and the decelerating of that motor and for the preferred embodiment is 200 steps as designated by N(5) in FIG. 2 where N(0) is designated as 0 steps. The last phase of the deceleration illustrated at 110 is selected to have a fixed number of steps therein (for the preferred embodiment it is 6 steps). The number of steps (N(5)−N(4))=6 as well as the deceleration rate (A(4) the preferred rate being −57,811 steps/sec$^2$) is selected experimentally so as to minimize the excess fluid pumped from the delivery pump 52 in the event that the check valve 54 should open early. The desired final stepping rate at 112 is also known. With these facts as well as the maximum deceleration A(3) (−320,000 step/sec in the preferred embodiment) during the decelerating region at 108 being known, the times T(3), T(4) and T(5) are easily calculated by the system control circuitry 22 so that all the specified requirements are achieved for any value of step rates at 100 and at 112.

Figure 3:
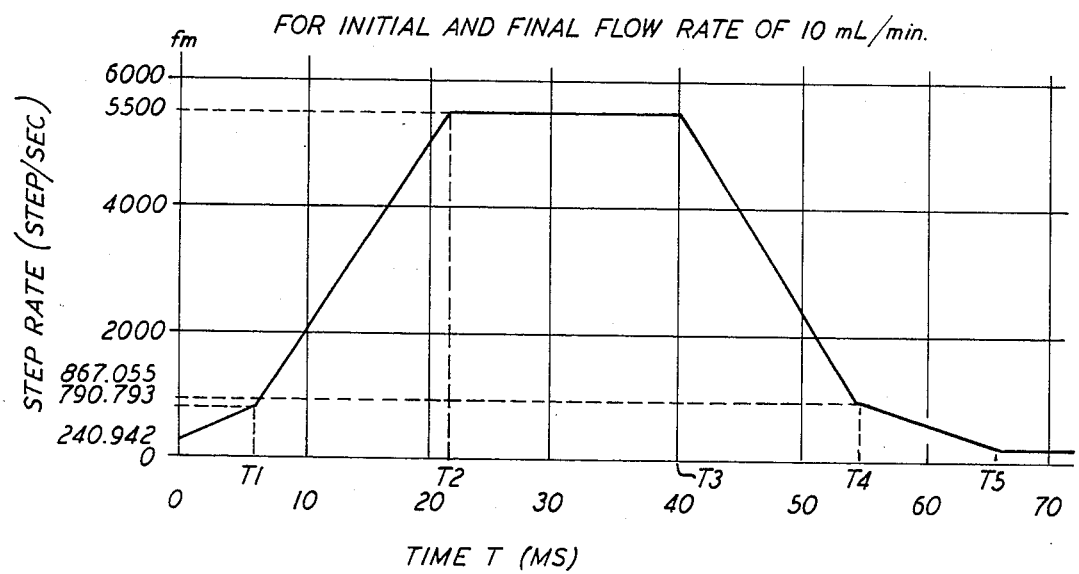
FIG. 3 and Table 1 show the step rate vs. time graph for the refill where the desired column flow rate is 1.0 mL/min.

Referring to FIG. 3 and Table 1, the operational characteristics for the stepping motor of the preferred embodiment of the present invention are shown where the desired column flow rate is 1.0 mL/min. At time TØ, the motor 26 step rate is 240.942 step/sec. During the time TØ to T1, the step rate accelerates at 94,550 step/sec$^2$ and reaches a rate of 790,793 step/sec at time T1. Then the step rate accelerates at a rate of 293,105 step/sec$^2$ from time T1 to T2. At time T2 the step rate goes to a constant of 5,500 steps/sec until time T3. At time T3, the motor 26 begins to slow down at a rate of −320,000 step/sec$^2$ until time T4. Then the rate of deceleration is slowed to −57,811 step/sec$^2$ until the motor reaches its final speed of 240.942 step/sec. This slowing the motor to a slow deceleration from time T4 to T5 serves to prevent pressure peaks at the column caused by some randomness in the reverse flow volume required to seat check valve 50.

Figure 4:
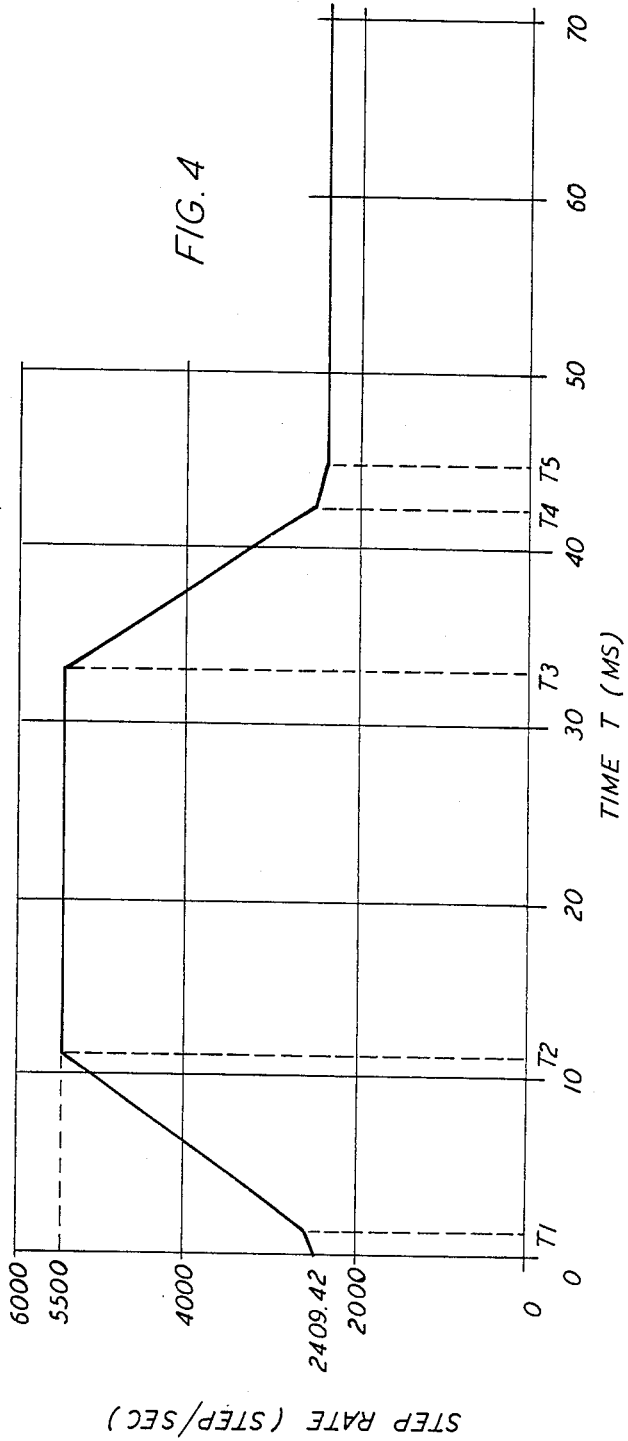
FIG. 4 and Table 2 show the step rate vs. time graph for the refill where the desired column flow rate is 10.0 mL min.

In a similar manner the illustrated motor drive characteristics are illustrated in FIG. 4 and Table 2 for a column flow rate of 10 mL/min. The acceleration rates are the same as for the corresponding time periods of FIG. 3. The length of time each curve segment occupies is different, however, the area under each of the curves between time TØ and T5 is the same since N(5) is fixed regardless of flow rate maintained in the column prior to and after the refill.

Figure 5:
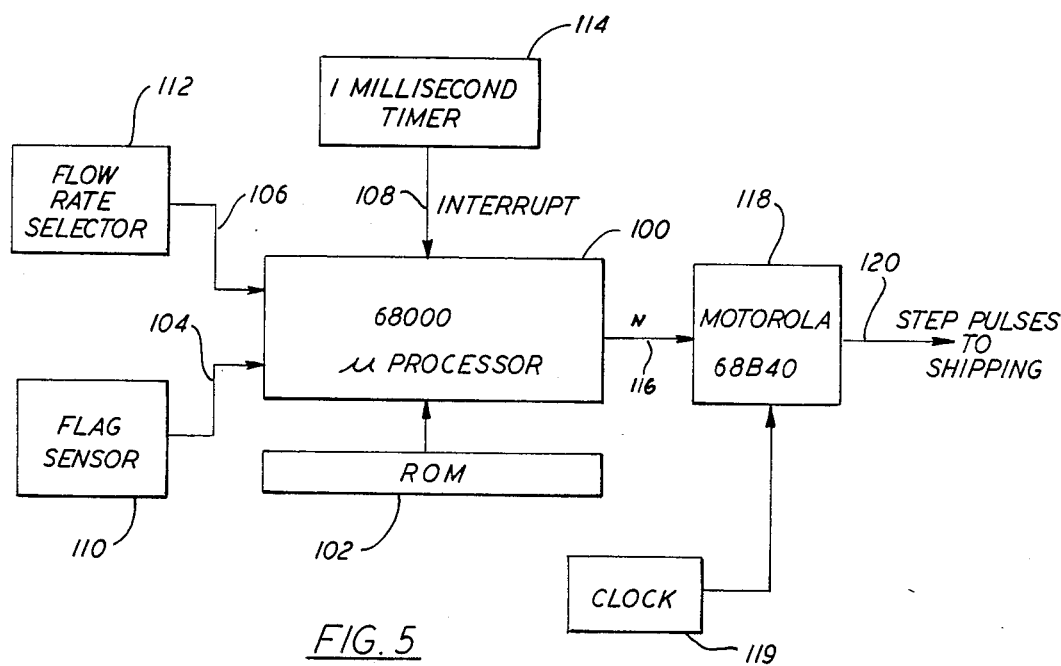
FIG. 5 is a block diagram of the circuitry of the preferred embodiment of the present invention.

The system control circuitry 22 of FIG. 1, is operative to produce the pulses on line 24 to the stepper motor 26 so as to provide the specific curves of FIGS. 3 and 4 for the plot of motor step rate vs. time. The system control circuitry 22 is illustrated in greater detail in FIG. 5. The control circuitry 22 includes a microprocessor 100 which, in the preferred embodiment, comprises a 68000 microprocessor from Motorola although other microprocessors may be utilized. Coupled to the microprocessor 100 is a Read Only Memory (ROM) 102 which controls the microprocessor 100 operation in a conventional manner. The microprocessor 100 also has input lines 104, 106 and 108 respectively from a flag sensor 110, which corresponds to the sensor 62 of FIG. 1, a flow rate selector 112 and an interrupt time 114. As previously noted, the flag sensor 110 produces a signal on line 104 when the flag on the shaft coupled to the motor is sensed. This signal advises the microprocessor that the refill should begin. Thereafter, each time the 1 millisecond timer 114 produces an interrupt (one interrupt occurs every millisecond) on line 108, the microprocessor responds thereto by producing, under ROM 102 control, a number N on line 116 which is sent to the pulse generator 118 which divides the clock 119 frequency and produces pulses on its output line 120 at a rate specified by the number N.

The number N is calculated previously by the microprocessor 100. The calculations are easily performed. Once the flow rate is determined, all the points on the curve of the type illustrated in FIGS. 3 and 4 can be calculated. The flow rate is multiplied by an adjustable scale factor (K) which is selected to give the correct number of pulses per second to the stepping motor required to produce the desired flow rate.

The acceleration of the pulse rate for each segment of the curve of the type shown in FIGS. 3 or 4 is known. Also the number of steps for the initial and the final segments are known. Thus the step rate at the end of the first curve segment F(1) is determined as follows: $F(1) = \sqrt{(F(0)^2 + 2(A(1))(N(1))}$ where F(0) is the initial step rate at T(0), A(1) is the acceleration in segment 1 (94,550 step/sec$^2$) and N(1) is the number of motor steps in the first curve segment which, for the preferred embodiment, is 3 and N(0)=0.

From the value for F(1) the time T1 which marks the end of the first segment is determined by the following equation: $T(1) = T(0) + (F(1) - F(0))/A(1)$.

In the second segment, the acceleration of the step rate is A(2)=293,105 and the maximum motor step rate is F(2)=5,500 step/sec. From this data and that previously calculated, the time T(2) at which the maximum velocity for the step motor is reached is determined by the equation: $T(2) = T(1) + (F(2) - F(1))/A(2)$. The total number of motor steps N(2) that have elapsed since the beginning of the refill is calculated from the equation: $N(2) = N(1) + (T(2) - T(1))(F(2) + F(1))/2$.

To complete the curve definition from this point one must work backward from the end point at time T(5) which occurs after N(5) pulses to the stepper motor at which time the motor speed is F(5) step/sec. The step rate F(4) at time T(4) is determined by the equation: $F(4) = \sqrt{(F(5))^2 + 2(A(5))M}$ where M is piston position impact margin in steps which is the number of steps in the last segment. N(5) is defined to be large enough so that the refill is complete and the pumping pressure is raised to the column pressure. In the preferred embodiment M=6 and N(5)=206.

After computing F(4), it is an easy matter to calculate N(3) from the equation: $N(3) = N(4) - ((F(3))^2 - (F(4))^2)/2/A(4)$ where F(3)=F(2) and A(4)=+320,000. The the times T(3), T(4) and T(5) can be calculated from the following equations:

$$T(3) = T(2) + (N(3) - N(2))/F(3)$$

$$T(4) = T(3) + (F(3) - F(4))/A(4)$$

$$T(5) = T(4) + (F(4) - F(5))/A(5)$$

Once the above equations have been solved, all the critical points on the curve of the type illustrated in FIG. 3 are known. Then, the microprocessor generates a table for the pulse rate to the stepper motor as a function of the time after the start of the refill. A point in the table is generated for each millisecond from the time of the start of the refill until the pump resumes pumping at the desired rate.

Once the lookup table is established for a given column flow rate, the microprocessor thereafter responds to the flag sensed signal from the flag sensor 110 to start the refill. Thereafter each 1 millisecond interrupt from the interrupt timer 114 causes the microprocessor 100 to look up a number N corresponding to the pulse rate in the table which corresponds to the number of interrupts occurring after the start of the refill. The number N is then sent to the setable pulse generator 118 which thereafter produces step pulses at the rate corresponding to N to the stepping motor.

When the flow rate selector 112 changes, the microprocessor 100 calculates a look up table for the one refill cycle where the initial step pulse rate is different from that at the end of the refill cycle. The microprocessor 100 also calculates the look up table for the new steady state refill cycle where the step rate is that selected by the selector 112 both at the beginning and at the end of the refill cycle. This second look up table is used following the delivery pump having pumped its contents for the first time into the column at the newly selected flow rate. The second look up table is used until the flow rate selector 112 changes again.

The above description has concentrated on the preferred embodiment of the present invention. However, it will be clear to those of skill in the art that modifications can be made to the described implementation of the present invention without departing from the spirit and scope of the present invention as defined in the claims.

What is claimed is:

1. A liquid pump motor control for use in a liquid chromatograph comprising, in combination:

a piston pump;

a stepping motor having a drive shaft for driving said piston pump;

an adjustable frequency pulse source coupled to said stepping motor to turn said stepping motor with the pulses from said pulse source;

a position scanning circuit coupled to the drive shaft of the stepping motor to sense when said drive shaft is at a position indicating that said pump should be refilled;

control means responsive to said position sensing circuit when the pump needs to be refilled to gradually accelerate at a first acceleration rate the pulses from said pulse source for the time required to produce $N_1$ pulses where $N_1$ is an integer, said control means after said $N_1$ pulses have been produced being operative to more rapidly accelerate, at a second rate greater than said first rate, the pulses from said pulse source until said pulses are at a maximum selected rate, said control means being further operative thereafter to maintain the pulses from said pulse source at said maximum selected rate for a selected number of pulses, said control means thereafter being operative to decelerate at a first deceleration rate the pulses from said pulse source until the pulses are at a selected rate, said control means thereafter being operative to decelerate the pulses from said pulse source at a second and lower deceleration rate than said first deceleration rate for a given number of pulses $N_5$, where $N_5$ is an integer, said pulse source reaching and remaining at said desired pulse rate until said position scanning circuit indicates said pump should be refilled, the number of pulses occurring between the start of pulse rate acceleration and the end of pulse rate deceleration being selectable and constant regardless of the pulse rate at the time said pump must be refilled or the final pulse rate after the second deceleration is complete.

2. The apparatus of claim 1 wherein said number of pulses occurring between the start of pulse rate acceleration and the end of pulse rate deceleration is 206.

3. The apparatus of claim 1 wherein $N_1$ is 3 steps.

4. The apparatus of claim 1 wherein $N_5$ is 6 steps.

5. The apparatus of claim 1 wherein said second acceleration rate is substantially the maximum rate of acceleration of pulses to said stepping motor which is possible without loosing synchronism between said stepping motor and the pulses applied thereto.

6. The apparatus of claim 1 wherein said first deceleration rate is substantially the maximum rate of deceleration of pulses to said stepping motor which is possible without losing synchronism between said stepping motor and the pulses applied thereto.

7. A chromatograph pumping apparatus comprising
a positive displacement delivery pump means having a cylinder, a delivery piston mounted for reciprocation therein, an inlet port adapted for interconnection to a metering pump means, and an outlet port adapted for interconnection to a chromatograph column,
a stepping motor having a drive shaft adapted for driving said delivery pump means,
means responsive to the rotation of said drive shaft for reciprocating said delivery piston for a relatively slow advance stroke and rapid retraction stroke,
a positive displacement metering pump means having a cylinder, a metering piston mounted for reciprocation therein, an inlet port adapted for interconnection to a supply of liquids, and an outlet port interconnected to said delivery pump means,
means for synchronously imparting reciprocating motion to said metering piston 180° out of phase with said delivery piston,
an adjustable frequency pulse source coupled to said stepping motor to turn said stepping motor with the pulses from said pulse source;
means for sensing when said drive shaft is at a position indicating that said delivery pump means should be refilled by said metering pump means; and
control means responsive to said sensing means when the delivery means needs to be refilled to gradually accelerate at a first acceleration rate the pulses from said pulse source for the time required to produce $N_1$ pulses where $N_1$ is an integer, said control means after said $N_1$ pulses have been produced being operative to more rapidly accelerate, at a second rate greater than said first rate, the pulses from said pulse source until said pulses are at a maximum selected rate, said control means being further operative thereafter to maintain the pulses from said pulse source at said maximum selected rate for a selected number of pulses, said control means thereafter being operative to decelerate at a first deceleration rate the pulses from said pulse source until the pulses are at a selected rate, said control means thereafter being operative to decelerate the pulses from said pulse source at a second and lower deceleration rate than said first deceleration rate for a given number of pulses $N_5$, where $N_5$ is an integer, said pulse source reaching and remaining at said desired pulse rate until said sensing means indicates said delivery pump means should be refilled, the number of pulses occurring between the start of pulse rate acceleration and the end of pulse rate deceleration being selectable and constant regardless of the pulse rate at the time said delivery pump means must be refilled or the final pulse rate after the second deceleration is complete.

8. The apparatus of claim 7 wherein said means for synchronously imparting reciprocating motion comprises mechanical linkage means for connecting said delivery piston and said metering piston for imparting the reciprocating movement of said delivery piston to said metering piston 180° out of phase with said delivery piston.

9. The apparatus of claim 7 wherein said number of pulses occurring between the start of pulse rate acceleration and the end of pulse rate deceleration is 206.

10. The apparatus of claim 7 wherein $N_1$ is 3 steps.

11. The apparatus of claim 7 wherein $N_5$ is 6 steps.

12. The apparatus of claim 7 wherein said second acceleration rate is substantially the maximum rate of acceleration of pulses to said stepping motor which is possible without loosing synchronism between said stepping motor and the pulses applied thereto.

13. The apparatus of claim 7 wherein said first deceleration rate is substantially the maximum rate of deceleration of pulses to said stepping motor which is possible without losing synchronism between said stepping motor and the pulses applied thereto.

14. The apparatus of claim 7 wherein said means for reciprocating said delivery piston comprises a cam operationally interconnected to said drive shaft and said delivery piston with a cam surface profile determinative of the displacement pattern of said delivery piston, said cam surface profile having a first portion for causing rapid retraction of the delivery piston occurring over a small fraction of a single revolution of said cam and a second portion for causing a relatively slower and uniform rate of advancement of the delivery piston.

15. The apparatus of claim 14 which comprises
a cam follower connected to said delivery piston to operationally engage said cam surface and
follower spring means for biasing said cam follower against the cam surface,
said cam surface profile having a hump portion between said first and second portions with said cam follower engaging said hump portion as the direction of the delivery piston reverses from advancement to retraction,
said control means accelerating said pulses at said first acceleration rate when said cam follower is engaging said hump portion to insure that the cam follower rides over said hump portion and at said second acceleration rate when said cam follower travels from said hump portion to said first portion so that the bias of said follower spring assists said stepping motor in accelerating said cam.

16. The apparatus of claim 14 which comprises
a cam follower connected to said delivery piston to operationally engage said cam surface and
follower spring means for biasing said cam follower against the cam surface,
said control means accelerating said pulses at said second acceleration rate when said cam follower initially engages said first portion of said cam surface.

17. A method for controlling the stepping motor which drives a liquid chromatograph pump during the refill of the pump comprising the steps of:

selecting a selected speed for the stepping motor to be used during pumping;

detecting the beginning of the pump refill cycle;

increasing the pulse rate to the stepping motor from said selected speed at a first acceleration rate for $N_1$ pulses where $N_1$ is an integer;

increasing the pulse rate to the stepping motor at a second acceleration rate greater than said first acceleration rate until a maximum desired pulse rate is obtained after $N_2$ pulses where $N_2$ is an integer;

maintaining the pulse rate to the stepping motor at said maximum pulse rate for $N_3$ pulses where $N_3$ is an integer;

decelerating at a first deceleration rate the pulses to the stepping motor for $N_4$ pulses, where $N_4$ is an integer, whereat the speed of the stepping motor is close to said selected speed;

decelerating at a second deceleration rate lower than said first deceleration rate for $N_5$ pulses, where $N_5$ is an integer, whereat the speed of the stepping motor is said selected speed;

maintaining the stepping motor at said selected speed until the beginning of the next refill cycle is detected;

the sum of $N_1+N_2+N_3+N_4+N_5$ being a constant regardless of said selected speed.

18. The method of claim 17 wherein said sum of $N_1+N_2+N_3+N_4+N_5$ is 206 steps.

19. The method of claim 17 where $N_1$ is 3 steps.

20. The method of claim 17 wherein $N_5$ is 6 steps.

21. The method of claim 17 wherein said second acceleration rate is substantially the maximum acceleration possible for the stepping motor and pump coupled thereto without any loss of synchronization between the stepping motor and the pulses applied thereto.

22. The method of claim 17 wherein said first deceleration rate is substantially the maximum deceleration possible for the stepping motor and the pump coupled thereto without loss of synchronization between the stepping motor and the pulses applied thereto.

* * * * *